United States Patent [19]
Nishi et al.

[11] Patent Number: 5,204,331
[45] Date of Patent: Apr. 20, 1993

[54] COMPOSITION FOR DEBRIDEMENT OF RETAINED LENS MATERIALS

[75] Inventors: Okihiro Nishi; Kayo Nishi, both of Osaka, Japan

[73] Assignee: Santen Pharmaceutical Co., Ltd., Osaka, Japan

[21] Appl. No.: 723,072

[22] Filed: Jun. 28, 1991

[30] Foreign Application Priority Data

Jun. 29, 1990 [JP] Japan ................................. 2-172914

[51] Int. Cl.$^5$ ..................... A61K 31/715; A61K 31/19
[52] U.S. Cl. ...................................... 514/54; 514/574; 514/912
[58] Field of Search ................................... 514/54, 574

[56] References Cited

PUBLICATIONS

Medline Abstract 88269479 (1988) Humphry et al.

Primary Examiner—Frederick E. Waddell
Assistant Examiner—Zohreh A. Fay
Attorney, Agent, or Firm—Armstrong & Kubovcik

[57] ABSTRACT

A composition for debridement of retained lens materials is disclosed. The composition comprises a viscoelastic material and ethylenediaminetetraacetic acid or salts thereof dissolved in a physiologically acceptable solution.

Preferably the viscoelastic material is sodium hyaluronate.

9 Claims, No Drawings

COMPOSITION FOR DEBRIDEMENT OF RETAINED LENS MATERIALS

FIELD OF THE INVENTION

The present invention relates to a novel composition which is useful for debridement of retained lens materials such as lens epithelial cells by an aspiration during a cataract surgery.

DESCRIPTION OF THE PRIOR ART

Cataract, frequently in aged people, is an intractable eye disease and various studies on a treatment of cataract have been made. But at present, the treatment of cataract is finally attained by surgical operations. Cataract surgery has been applied for a long time and various operative methods have been examined. In such operative methods, there are problems how to easily and completely extract an opaque lens, how to prevent postoperative complications, and how to fast and satisfactorily recover from operative damages.

Recently a phacoemulsification procedure is getting widely used to extract the opaque lens. The procedure consists of applying supersonic waves to the cataract in a lens capsule to emulsify it and removing it by aspiration. The procedure has merits that complications caused by a large incision are few and the recovery from operation damages is fast because the incised wound is small.

Formerly, after cataract extraction, the visual acuity of the patient was improved by applying glasses or contact lens, but recently it is widely applied to recover the visual acuity by implanting an intraocular lens.

The phacoemulsification procedure is very useful to extract an opaque lens, however, it needs high technology to remove the retained lens materials such as lens epithelial cells without damaging intraocular tissues.

Lens epithelial cells have self-proliferating abilities. If the cells remain after an operation, they cause postoperative complications such as secondary cataract, residual capsular opacification, intraocular lens dislocation, fibrin reaction and phacoanaphylactic endophthalmitis. They can be prevented by thorough removal of the lens epithelial cells.

The methods for lens epithelial cell removal can be classified in mechanical means and pharmaceutical means. As a pharmaceutical method, use of ethylenediaminetetraacetic acid (EDTA) is reported as successful. (Brit. J. Ophthalmol., 72 406–408 (1988)). EDTA is used for separating cells in tissue culture. It loosens junctional complex of cells. However, influences of EDTA on intraocular tissues have to be considered.

First, it is an influence on corneal endothelial cells. If intercellular junctions are damaged, the functions of corneal epithelial cells can be decompensated, resulting in corneal edema, opaque, etc. If zonules are damaged and partially dissolved by EDTA, a posterior chamber intraocular lens may dislocate or luxate. If zonules are dissolved completely, an implantation of an intraocular lens becomes impossible because a sustaining tissue, namely a lens capsule, disappears. Even if an intraocular lens can be implanted, there exists a high risk to dislocate after an operation. Therefore, it needs to study how to keep EDTA in the lens capsule, namely, how to prevent the leakage of EDTA from the capsular opening incised to remove the cataracts.

We found that leakage of EDTA from the opening of the lens capsule can be prevented effectively, when EDTA is mixed with a viscoelastic material with high molecular weight and viscosity, and the mixture is injected into the lens capsule after removal of cataractous lens by endocapsular phacoemulsification procedure with a small anterior capsulotomy.

SUMMARY OF THE INVENTION

The object of the present invention is to provide a method for treating cataract for debridment of retained lens epithelial cells without leakage of EDTA or salts thereof from anterior capsular opening that is needed for removing cataract.

The other object of this invention is to provide a pharmaceutical composition which is used in above mentioned treating method.

The inventors, having strenuously studied to achieve the above-mentioned object, have found the fact that when EDTA or salts thereof and viscoelastic material both dissolved in a physiologically acceptable solution are injected into the capsular bag after cataract extraction by endocapsular phacoemulsification-aspiration following the small anterior capsulotomy, EDTA or salts thereof can be effectively prevented from leaking out the capsular bag through the incised opening. EDTA or salts thereof does not leak out of the capsular bag so much to influence the intraocular tissues, and the lens epithelial cells which are difficult to sufficiently be removed even with the phacoemulsification-aspiration can be removed even with a low level of aspiration power.

Retained lens materials are various substances remaining in the lens capsule during a cataract surgery, and the representative example of them is lens epithelial cells.

According to the present invention we provide a composition for debridement of retained lens materials, especially lens epithelial cells, comprising a viscoelastic material and EDTA or salts thereof both dissolved in a physiologically acceptable solution.

Preferably the viscoelastic material is sodium hyaluronate.

DESCRIPTION OF THE PREFERRED EMBODIMENT

Preferable salts of EDTA in this invention are disodium salt, trisodium salt and tetrasodium salt, and a more preferable salt is disodium salt.

The concentration of EDTA or salts thereof in the solution can be defined according to the binding strength of lens epithelial cells differing from patient to patient. The preferable concentration is 5 to 50 millimol/l, (hereinafter referred to as mM).

As the viscoelastic material, clinically applied high molecular materials can be used. Preferable examples of such materials are hyaluronic acid or salts thereof, methylcellulose, hydroxymethylcellulose, carboxyvinyl polymer, polyvinylpyrrolidone, polyvinylalcohol, polyacrylamide, kitin and collagen. In view of a protection of eye tissues, sodium hyaluronate is more preferable.

The above mentioned viscoelastic material is used in the form of physiologically acceptable solutions. The concentration of the viscoelastic material in the solutions is selected according to the desired viscosity, and usually 0.1 to 5% by weight, preferably 0.5 to 3.0% by weight. As the solution of the viscoelastic material, aqueous solution of sodium hyaluronate is widely used in ophthalmologic surgeries, and is preferable because of its protection effects on eye tissues. The molecular weight of sodium hyaluronate is not limited but selected according to the desired viscosity, and is in the range of about 600,000 to 4,000,000, preferably 800,000 to 3,000,000. The viscosity of sodium hyaluronate solution depends on its concentration and molecular weights, and is 2,000 to 200,000 cP, preferably 10,000 to 100,000 cP.

The pH value of the preparations according to the present invention may be that ophthalmologically applied, and preferably in the range of 4 to 8.

No special technology is required for making the preparations of this invention. For example, EDTA or salts thereof and the viscoelastic material such as sodium hyaluronate are dissolved in a physiologically acceptable solution to make the preparations, and if necessary pharmaceutically acceptable excipients, buffers, pH adjusting agent etc. can be added. Examples of the physiologically acceptable solution are isotonic sodium chloride solution, distilled water for injection adjusted to physiological condition by adding isotonic agents such as sodium chloride and potassium chloride, and balanced salt solution (BSS).

A typical method of clinically applying the pharmaceutical composition according to the present invention will be briefly described in the following.

After the anterior lens capsule of a cataract patient is incised to form a small opening, and the cataractous lens materials are removed with phacoemulsification-aspiration procedure, the preparation of this invention is injected through the capsular opening. Two minutes after the injection, the retained lens materials including lens epithelial cells are removed together with the preparation while the interior of the capsule being irrigated with an irrigation solution. The amount of the injected preparation can be selected according to the volume of the patient's lens capsule (about 0.2 ml).

This invention affords the following effects or advantages.

On a cataract surgery, lens epithelial cells can be easily removed by injecting the composition according to the present invention into the capsular bag. Furthermore, leakage of EDTA or salts thereof from capsular opening can be effectively prevented by an application of EDTA or salts thereof with viscoelastic material.

This invention offers a medical preparations which is effective in easy and complete debridement of retained lens materials such as lens epithelial cells by an aspiration during a cataract surgery.

EXAMPLES

Examples of preparations applying sodium hyaluronate and disodium ethylenediaminetetraacetate will be shown in the following.

PREPARATIONS EXAMPLES

| Formula 1: | |
|---|---|
| Sodium hyaluronate (molecular weight 1.8 to 2.2 million) | 1.5 g |
| Disodium ethylenediaminetetraacetate | 0.33 g |
| Sodium chloride | 0.9 g |
| Distilled water for injection | q.s. |
| Total | 100 ml |

Process of preparation:

Disodium ethylenediaminetetraacetate and optionally sodium chloride were dissolved in distilled water for injection, and then to the solution was added sodium hyaluronate to make the preparations. Preparations of Formulas 2 to 9 were also made in the same manner.

| Formula 2: | |
|---|---|
| Sodium hyaluronate (molecular weight 1.8 to 2.2 million) | 1.0 g |
| Disodium ethylenediaminetetraacetate | 0.168 g |
| Sodium chloride | 0.9 g |
| Distilled water for injection | q.s. |
| Total | 100 ml |

| Formula 3: | |
|---|---|
| Sodium hyaluronate (molecular weight 1.8 to 2.2 million) | 2.0 g |
| Disodium ethylenediaminetetraacetate | 1.68 g |
| Sodium chloride | 0.9 g |
| Distilled water for injection | q.s. |
| Total | 100 ml |

| Formula 4: | |
|---|---|
| Sodium hyaluronate (molecular weight 1.9 to 3.9 million) | 0.5 g |
| Disodium ethylenediaminetetraacetate | 0.68 g |
| Distilled water for injection | q.s. |
| Total | 100 ml |

| Formula 5: | |
|---|---|
| Sodium hyaluronate (molecular weight 1.9 to 3.9 million) | 1.5 g |
| Disodium ethylenediaminetetraacetate | 0.336 g |
| Distilled water for injection | q.s. |
| Total | 100 ml |

| Formula 6: | |
|---|---|
| Sodium hyaluronate (molecular weight 0.6 to 1.2 million) | 2.5 g |
| Disodium ethylenediaminetetraacetate | 0.336 g |
| Sodium hydrogenphosphate | 0.05 g |
| Sodium dihydrogenphosphate | q.s. |
| Distilled water for injection | q.s. |
| Total | 100 ml |

| Formula 7: | |
|---|---|
| Sodium hyaluronate (molecular weight 0.6 to 1.2 million) | 3.0 g |
| Disodium ethylenediaminetetraacetate | 0.336 g |
| Distilled water for injection | q.s. |
| Total | 100 ml |

| Formula 8: | |
|---|---|
| Sodium hyaluronate (molecular weight 0.6 to 1.2 million) | 2.0 g |
| Disodium ethylenediaminetetraacetate | 0.336 g |
| Distilled water for injection | q.s. |
| Total | 100 ml |

| Formula 9: | |
|---|---|
| Sodium hyaluronate (molecular weight 0.6 to 1.2 million) | 1.5 g |
| Disodium ethylenediaminetetraacetate | 0.336 g |
| Distilled water for injection | q.s. |
| Total | 100 ml |

| Formula 10: | |
|---|---|
| Sodium hyaluronate (molecular weight 1.8 to 2.2 million) | 1.5 g |
| Disodium ethylenediaminetetraacetate | 0.336 g |
| Isotonic sodium chloride solution | q.s. |
| Total | 100 ml |

Process of preparation:

Disodium ethylenediaminetetraacetate was disoloved in isotonic sodium chloride solution, and then to the solution was added sodium hyaluronate to make the preparations. Preparations of Formulas 11 to 14 were also made in the same manner.

| Formula 11: | |
| --- | --- |
| Sodium hyaluronate (molecular weight 1.8 to 2.2 million) | 1.5 g |
| Disodium ethylenediaminetetraacetate | 0.235 g |
| Isotonic sodium chloride solution | q.s. |
| Total | 100 ml |

| Formula 12: | |
| --- | --- |
| Sodium hyaluronate (molecular weight 1.8 to 2.2 million) | 1.5 g |
| Disodium ethylenediaminetetraacetate | 0.504 g |
| Isotonic sodium chloride solution | q.s. |
| Total | 100 ml |

| Formula 13: | |
| --- | --- |
| Sodium hyaluronate (molecular weight 1.8 to 2.2 million) | 1.5 g |
| Disodium ethylenediaminetetraacetate | 1.009 g |
| Isotonic sodium chloride solution | q.s. |
| Total | 100 ml |

| Formula 14: | |
| --- | --- |
| Sodium hyaluronate (molecular weight 1.8 to 2.2 million) | 1.5 g |
| Disodium ethylenediaminetetraacetate | 1.513 g |
| Isotonic sodium chloride solution | q.s. |
| Total | 100 ml |

| Formula 15: | |
| --- | --- |
| Sodium hyaluronate (molecular weight 1.8 to 2.2 million) | 1.5 g |
| Disodium ethylenediaminetetraacetate | 0.672 g |
| BSS | q.s. |
| Total | 100 ml |

Process of preparation:

Disodium ethylenediaminetetraacetate was dissoloved in BSS, and then to the solution was added sodium hyaluronate to make the preparations. Preparations of Formula 16 was also made in the same manner.

| Formula 16: | |
| --- | --- |
| Sodium hyaluronate (molecular weight 0.8 to 1.8 million) | 1.5 g |
| Disodium ethylenediaminetetraacetate BSS | q.s. |
| Total | 100 ml |

EXPERIMENT

EXPERIMENTAL EXAMPLE 1

We examined the effect of disodium ethylenediaminetetraacetate, dissolved in an aqueous solution of sodium hyaluronate, a typical viscoelastic substance, on human lens epithelial cells.

Experimental Method

A piece of anterior lens capsule (diameter: 5 to 6 mm), obtained by circular capsulotomy during cataract surgery was preserved in MEM media. The piece was soaked for 2 minutes in isotonic sodium chloride solution containing disodium ethylenediaminetetraacetate and 1.5% by weight sodium hyaluronate (molecular weight: about 2 million). The piece was picked up by a pincette and washed with 10 ml of water by a syringe. The remaining extent of lens epithelial cells was observed by an inverted phase contrast microscope.

As a control, a piece soaked in 1.5% by weight sodium hyaluronate dissolved in isotonic sodium chloride solution without disodium ethylenediaminetetraacetate was treated in the same manner as the above procedure.

Result

We examined the effect of disodium ethylenediaminetetraacetate in each concentration of 15 mM (two samples), 30 mM (two samples) or 45 mM (one sample). In all case, almost all of lens epithelial cells were stripped and no degeneration on the lens capsule itself was observed by a microscope.

On the other hand, in the control about 60% of lens epthelial cells remained.

EXPERIMENTAL EXAMPLE 2

We examined the remaining extent of lens epithelial cells using rabbit lens instead of human lens capsule as in Example 1.

A solution of disodium ethylenediaminetetraacetate and 1.5% sodium hyaluronate in isotonic sodium chloride solution was injectd into a lens capsule after an extraction of cataractous lens through a small anterior capsulotomy by endocapsular phacoemulsification procedure. After 2 minutes, lens endocapsular epithelial cells attached to the anterior capsule were aspirated off.

Result

We examined the effect of disodium ethylenediaminetetraacetate in each concentration of 5 mM, 7 mM or 10 mM. In case of 10 mM, almost all of epithelial cells were stripped. In case of 5 mM and 7 mM, small amount of epithelial cells remained. However, such remaining epithelial cells could be completely removed by weak aspiration.

EXPERIMENTAL EXAMPLE 3

A solution of disodium ethylenediaminetetraacetate (concentration: 10 mM) and 1.5% sodium hyaluronate in isotonic sodium chloride solution was injected into a lens capsule by the same manner as in Example 2. After 2 minutes, aqueous humor was sucked by a syringe and the amount of disodium ethylenediaminetetraacetate leaked into aqueous humor was measured.

As a control, disodium ethylenediaminetetraacetate (concentration; 10 mM) dissolved in isotonic sodium chloride solution was used in the same manner as above mentioned procedure.

Result

The leakage rates (%)=[(the amount of disodium ethylenediaminetetraacetate leaked into aqueous humor)÷(the amount of injected disodium ethylenediaminetetraacetate)×100] are shown in the following table.

TABLE

| | Leakage Rate (%) |
| --- | --- |
| Control | 19.5 (average of two samples) |
| Preparations of Formula 10 | 1.1 (average of three samples) |

As shown in the table, the leakage rate of the disodium ethylenediaminetetraacetate using sodium hyaluronate was nearly 0 in comparison with the fact that about 20% of the injected disodium ethylenediaminetetraacetate of the control was leaked, whereby the influences of the former on the peripheral intraocular tissues were negligible.

What is claimed is:

1. A composition for debridement of retained lens materials, comprising an effective amount of ethylenediaminetetraacetic acid (EDTA) or salts thereof and a viscoelastic material in an amount sufficient to prevent leakage of said EDTA or salts thereof from a lens capsule, both dissolved in a physiologically acceptable solution.

2. A composition as defined in claim 1, wherein the viscoelastic material is sodium hyaluronate.

3. A composition as defined in claim 2, wherein the viscosity of the solution containing the viscoelastic material and ethylenediaminetetraacetic acid or salts thereof is in the range of 10,000 to 100,000 cP.

4. A composition as defined in claim 2, wherein the molecular weight of the sodium hyaluronate is in the range of 600,000 to 4,000,000.

5. A composition as defined in claim 2, wherein the concentration of the ethylenediaminetetraacetic acid or salts thereof is in the range of 5 to 50 millimol/l.

6. A composition as defined in claim 2, wherein ethylenediaminetetraacetic acid salt is disodium ethylenediaminetetraacetate.

7. A composition for debridement of retained lens materials comprising a viscoelastic material and ethylenediaminetetraacetic acid or salts thereof both dissolved in a physiologically acceptable solution, the viscosity of the solution containing the viscoelastic material and ethylenediaminetetraacetic acid or salts thereof being 10,000 to 100,000 cP, and the concentration of the ethylenediaminetetraacetic acid or salts thereof being in the range of 5 to 50 millimol/l.

8. A composition for debridement of retained lens materials comprising sodium hyaluronate having a moleculer weight of 600,000 to 4,000,000, and ethylenediaminetetraacetic acid or salts thereof both dissoloved in a physiologically acceptable solution, the viscosity of the solution containing the viscoelastic material and ethylenediaminetetraacetic acid or salts thereof being 10,000 to 100,000 cP, and the concentration of the ethylenediaminetetraacetic acid or salts thereof being in the range of 5 to 50 millimol/l.

9. A method for debridement of retained lens materials remaining after a lens extraction from a cataract patient with phacoemulsification-aspiration procedure characterized in that the composition as defined in any one of claims 1 to 8 is injected in the lens capsule and thereafter the retained lens materials are extracted from the capsule.

* * * * *